US008367100B2

(12) United States Patent
Smith et al.

(10) Patent No.: US 8,367,100 B2
(45) Date of Patent: Feb. 5, 2013

(54) PREPARATION AND USE OF SLEEVE AND MICRO-ENCAPSULATED TOPICAL ANALGESIC PATCH FOR TREATING PAIN

(75) Inventors: Shane C Smith, Chattanooga, TN (US); Joseph Czerwinski, Chattanooga, TN (US); Mike Davies, Buford, GA (US); Don Moak, Chattanooga, TN (US); Blair Ramey, Chattanooga, TN (US)

(73) Assignee: Chattem, Inc., Chattanooga, TN (US)

( * ) Notice: Subject to any disclaimer, the term of this patent is extended or adjusted under 35 U.S.C. 154(b) by 83 days.

(21) Appl. No.: 12/862,423

(22) Filed: Aug. 24, 2010

(65) Prior Publication Data
US 2011/0004169 A1 Jan. 6, 2011

Related U.S. Application Data

(62) Division of application No. 10/844,690, filed on May 13, 2004, now Pat. No. 8,282,607.

(60) Provisional application No. 60/470,513, filed on May 14, 2003.

(51) Int. Cl.
*A61M 35/00* (2006.01)
*B65B 63/02* (2006.01)
*B65B 65/00* (2006.01)
*B65D 75/30* (2006.01)

(52) U.S. Cl. ............ 424/447; 604/290; 53/431; 53/438; 206/484.2

(58) Field of Classification Search .................. None
See application file for complete search history.

(56) References Cited

U.S. PATENT DOCUMENTS

| 4,435,180 | A | * | 3/1984 | Leeper | 424/402 |
|---|---|---|---|---|---|
| 5,227,165 | A | * | 7/1993 | Domb et al. | 424/450 |
| 5,758,659 | A | * | 6/1998 | Thompson | 128/844 |
| 7,012,169 | B2 | * | 3/2006 | McDevitt et al. | 602/41 |
| 2003/0135171 | A1 | * | 7/2003 | Ingram et al. | 604/308 |

OTHER PUBLICATIONS

Entry Term: KNIT. (2001) In Chambers 21$^{st}$ Century Dictionary.*

* cited by examiner

*Primary Examiner* — Robert A Wax
*Assistant Examiner* — Danah Al-Awadi
(74) *Attorney, Agent, or Firm* — Miller & Martin PLLC

(57) ABSTRACT

Novel micro-encapsulated topical analgesics are provided to treat pain and may be applied via sleeves having dosed therapeutic sections, especially to joints and extremities. Sleeves may be prepared and packaged inside-out and inverted when positioned by the wearer.

19 Claims, 4 Drawing Sheets

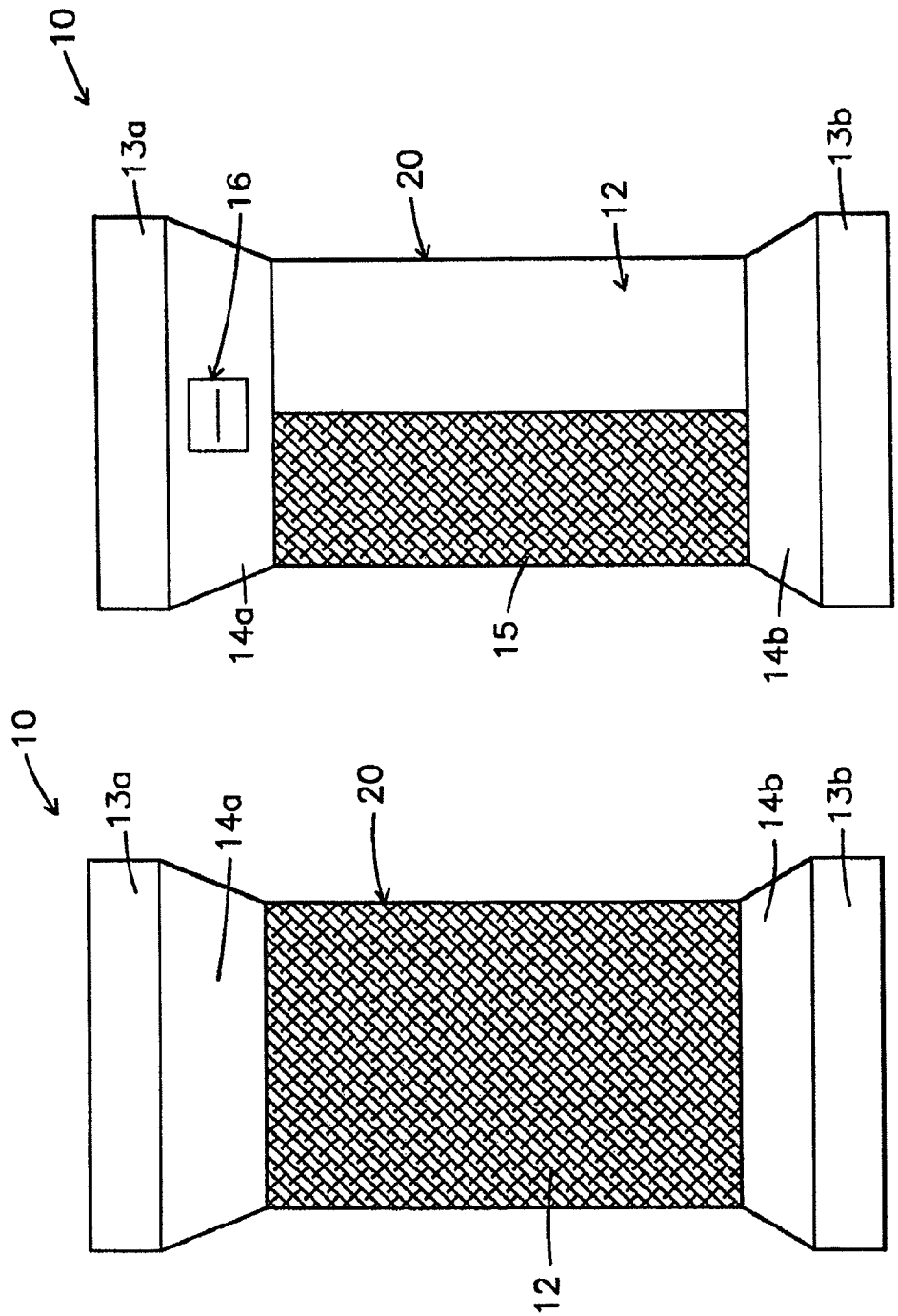

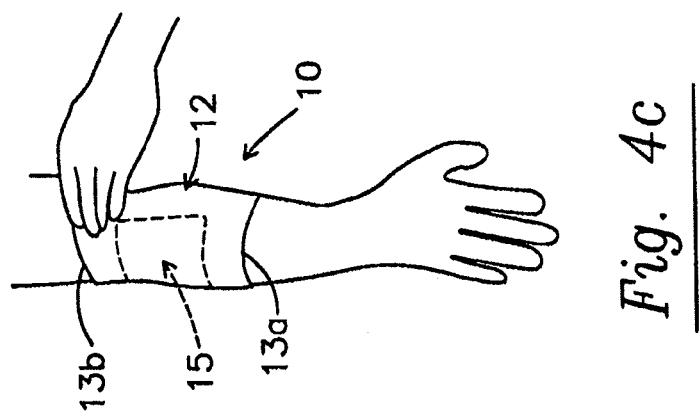
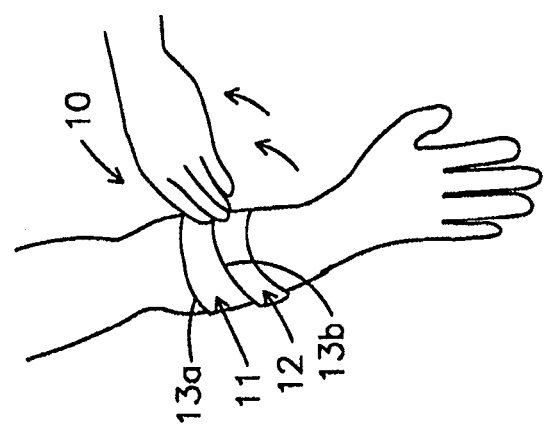
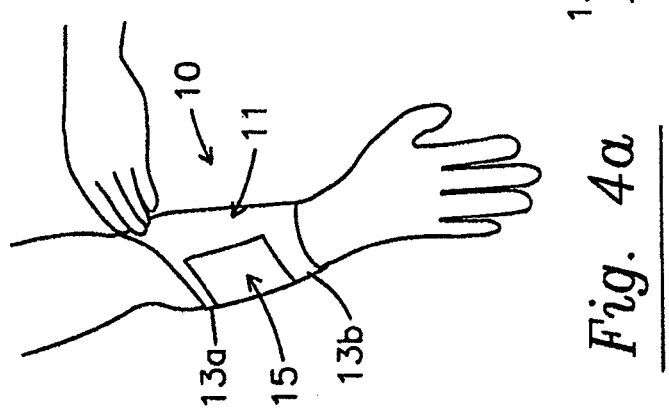

PREPARATION AND USE OF SLEEVE AND MICRO-ENCAPSULATED TOPICAL ANALGESIC PATCH FOR TREATING PAIN

The present invention is a divisional of application U.S. Ser. No. 10/844,690, filed May 13, 2004, now U.S. Pat. No. 8,282,607 which claims the benefit of the provisional application U.S. Ser. No. 60/470,513, filed May 14, 2003.

FIELD OF THE INVENTION

The present invention relates to a topical preparation used to reduce or treat pain, and a new sleeve used for application of topical preparations. The active ingredients of the topical preparation are micro-encapsulated to provide extended release of the active ingredients and improved feel and working characteristics of the preparation. The micro-encapsulated active ingredients are especially useful in connection with preparations applied via sleeves or patches, however, the encapsulated topical analgesic may be administered in the form of a cream, ointment, balm, stick, patch, sleeve or other forms used for topical application.

BACKGROUND OF THE INVENTION

Topical preparations in the form of analgesics are widely used to relieve pain. They are typically used by consumers with muscle or joint pains, soreness, sprains or strains, and are used by consumers unable to tolerate oral analgesics, for example users who suffer from ulcers or who are pregnant, or consumers desiring topical analgesia as an adjunct to oral medication. Topical analgesics typically come in the form of ointments, lotions, solutions and creams that are applied to the affected area. They relieve the pain and stiffness of arthritis, rheumatism, muscle and joint soreness, back pain, bursitis, tendonitis, muscle strains and sprains, bruises and cramps. In more recent years, topical analgesics have been administered via adhesive patches, particularly in cases of back aches and soreness.

Although topical analgesics are effective in providing prompt pain relief, their effect is not always long lasting. Some topical analgesics must be reapplied often because the effect wears off quickly. Topical analgesics may also be rubbed off during daily activities or wiped off by the rubbing of clothes against the affected area. Recently, patches consisting of topical analgesics have been used to realize longer lasting pain relief, such as described in U.S. Pat. No. 6,277,401, which teaches a patch for drug delivery through a foam layer. Many other topical analgesic patches are simply a layer of adhesive impregnated with a topical analgesic formulation and a layer of gauze or other fabric. These patches apply the active ingredients in the form of a semi-flexible patch that holds the analgesic and protects it from being worn off during daily activities. Although usually having longer efficacy than topical application of creams and ointments, the analgesic patches only minimally extend release of the active ingredients and so the effectiveness of the analgesic wears off quickly. Moreover, the patches have a number of draw backs. Consumers do not like the feel of the patches because they feel wet, often have strong menthol odors, and do not adhere well to joints. The application of the patches can also be difficult. Additionally, the patches do not stay in place, except when used on flat body areas such as the back, which are not subject to substantial movements or flexing actions. Finally, use of the patches on hirsute body areas may result in additional pain due to unintended hair extraction when the patch is removed.

Despite the existence of topical analgesic creams, lotions and sticks and topical analgesics in the form of patches in the prior art, there is room for improvement. None of the prior art discloses employing a micro-vesicle system for administration of the active ingredients in order to provide for extended release of the active ingredient resulting in more effective treatment. Use of the micro-vesicle technology may also reduce the wet and soggy feeling associated with the application of analgesic patches, because less ointment is required to achieve the desired effect. Moreover, the prior art does not disclose the use of topical analgesics in the form of sleeves or joint-specific applications so that the topical preparation stays in place through the full range of motion and repeated bending of a joint, and without the requirement of an adhesive to hold the patch in place.

A variety of methods are currently used to administer topical analgesics for pain relief. The methods typically involve the topical administration of analgesics to the affected area. Some products are administered in the form of creams, lotions, ointments and sticks. Although these products provide faster and more localized pain relief than the oral administration of drugs, the relief may be short lived if the analgesic is not long lasting or wears off quickly. Other products include patches impregnated with topical or external analgesics that are applied to the target area. Although these products provide longer lasting pain relief by holding the active ingredients, patches still do not provide substantially extended release of active ingredients and do not suitably adhere to joint areas. Removal of adhesive patches may also produce consumer discomfort. A more effective and long lasting method of administering these products is needed.

The current invention consists of a product for topical administration of extended release substances for relieving pain. The invention comprises micro-encapsulation of one or more active ingredients to provide extended release of the active ingredient in the form of a cream, lotion, ointment or stick. Alternatively, the invention may be in the form of a flexible patch or sleeve, or joint specific application, providing an extended release active formulation.

SUMMARY OF THE INVENTION

The present invention recognizes and addresses the foregoing disadvantages, and others, of prior art compositions and methods.

Briefly, the present invention is a novel topical preparation used to treat pain and improve joint function. The topical preparation consists of micro-encapsulated active ingredients to provide extended release of the active ingredients. The micro-encapsulated topical preparation may be administered in the form of a cream, lotion, solution, ointment, balm, stick, patch or other forms used for topical application. The present invention may also be used in connection with a sleeve so that the topical preparation is easy to apply and stays in place during the full range of motion and repeated bending of a joint, and without the requirement of an adhesive.

One novel aspect of the topical preparation of the present invention is the use of micro-encapsulated active ingredients for extended release of the active ingredients and long lasting relief.

Another novel aspect of the invention is the use of micro-vesicle technology to reduce the unpleasant wet and soggy feelings associated with the application of analgesic patches.

Another novel aspect of the present invention is the use of topical analgesics in the form of sleeves so that the topical analgesic is suitably positioned at joint areas and stays in place.

Another novel aspect of the present invention is the use of topical analgesics carried in the form of sleeves so that the topical analgesic carrier may be removed without producing the consumer discomfort of an adhesive carrier.

More particularly, it is an object of the present invention to provide a topical preparation with micro-encapsulated active ingredients in the form of a sleeve which is long lasting, easy to apply, and securely positioned at joint areas.

Additional objects and advantages of the invention will be set forth in part in the following description, or may be obvious from the description, or may be learned through the practice of the invention.

BRIEF DESCRIPTION OF THE DRAWINGS

Certain aspects of the invention may be better appreciated with reference to the following illustrations:

FIG. 1 is a top plan view of a sleeve according to the present invention with patch area adapted to receive a topical analgesic preparation in the form.

FIG. 2 is a side plan view of the sleeve of FIG. 1.

FIGS. 4a, 4b and 4c show the sequential application of the sleeve to the elbow.

DETAILED DESCRIPTION OF THE INVENTION

Figure 3B:
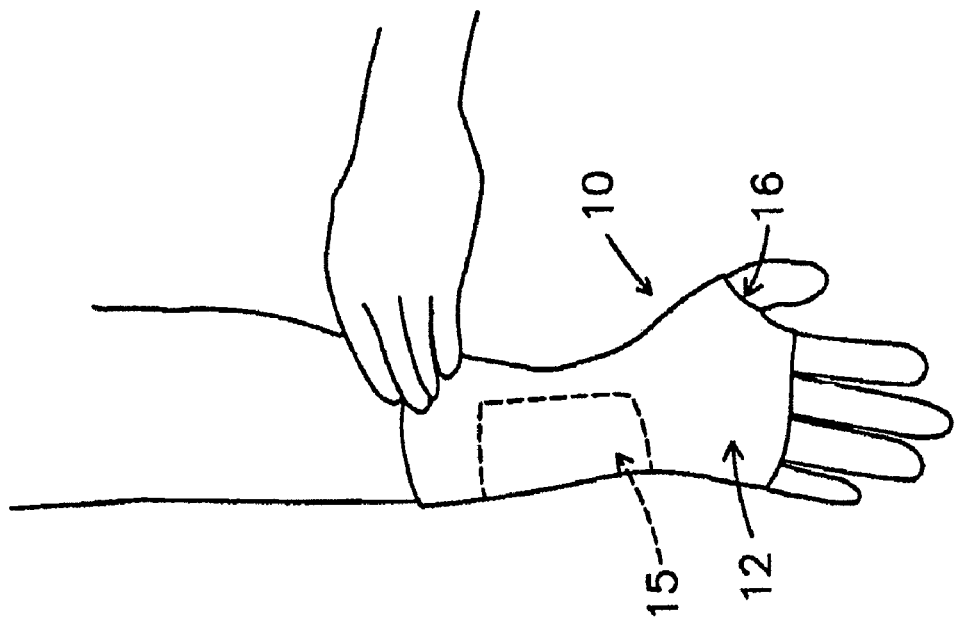
FIGS. 3a and 3b show the sequential application of the sleeve to the wrist.

This invention teaches a topical preparation for pain relief in humans and a flexible sleeve for application of topical preparations. The topical preparation contains a micro-encapsulated active ingredient formulation to provide extended release of the active ingredients for long lasting pain relief and improved touch and feel of the preparation to the consumer. The topical preparation may be in the form of a stick, cream, lotion, solution or ointment applied to the affected area. Alternately, the topical preparation may be administered in the form of an impregnated patch or sleeve. The micro-encapsulation of the active ingredient of the topical preparation provides immediate, and long lasting pain relief. In addition, the use of micro-encapsulated active ingredients tends to improve the feel of the entire preparation. The topical preparation may be used to reduce or treat pain, soreness or stiffness associated with arthritis, rheumatism, muscle and joint soreness, back pain, bursitis tendonitis, muscle strains and sprains, bruises and cramps.

A variety of topical analgesics may be used in connection with the present invention. The most common topical analgesics are local anesthetics and anti-inflammatories such as salicylates or NSAIDS, and counter-irritants including capsaicin and aromatic compounds. Anesthetics such as lidocaine, that act on local sensory afferents, are intended to totally block pain receptors and numb the area of application. Salicylates and NSAIDS such as ibuprofen, are anti-inflammatory compounds that inhibit pain and inflammation and are generally taken internally. Counter-irritants and aromatics, especially terpenes, are substances such as menthol, oil of wintergreen, camphor, eucalyptus, mustard plasters and turpentine oil, that mask sensations of pain by stimulating local pain afferents and thereby creating a feeling of cold or heat over the affected area. Capsaicin is a natural ingredient found in cayenne peppers. Capsaicin is believed to operate in an anesthetic fashion by depleting Substance-P from sensory afferents and thereby suppressing transmission of pain to the brain. Menthol is a compound obtained from peppermint oils, or other mint oils, or made synthetically. Menthol has local anesthetic and counterirritant qualities.

The preferred active ingredient of the present invention is menthol or menthol/menthyl derivatives, such as 1-menthol. Effective amounts of menthol range from 1.25% to 16% by weight of the preparation. Alternately, an effective amount of menthyl lactate may be used, usually between about 0.5% to 20% by weight of the preparation. Capsaicin, or other capsaicinoids, vanilloids, or vanillyl butyl ether, may also be used. The effective amount of capsaicin ranges from 0.025% to 0.25% by weight of the preparation.

The base formula can be any suitable carrier, anhydrous, water-based, an emulsion of either oil-in-water or water-in-oil, or alcohol. Additional or alternative ingredients may be used in the composition of the present invention, including, the external analgesic ingredients or combinations recognized in the Food and Drug Administration's External Analgesic Drug Products for Over-The-Counter Human Use; Tentative Final Monograph, published at 48 Federal Register, pp. 5852-5869, Feb. 8, 1983.

The form of furnishing the topical analgesic is novel to the field because it provides the active ingredient in a micro-encapsulated form which provides for extended release of the active ingredient and reduces the soggy wet feeling when the topical analgesic is held in the form of a patch. Micro-encapsulation can be achieved through liposome or NOVASOMES® brand technology. The preferred technology for micro-encapsulation is liposome based technology, without the use of phospholipids. This technology is used with products supplied by Novavax Inc. of Buena, N.J. under the NOVASOMES® brand. However, other methods of micro-encapsulation may be used. NOVASOMES® based technology generally uses non-phospholipid vesicles made from amphiphiles using a manufacturing process, in which drugs can be encapsulated for oral or topical delivery into the body. Amphiphiles include fatty alcohols and acids, ethoxylated fatty alcohols and acids, glycol esters of fatty acids, glycerol fatty acid anmono and diesters, ethoxylated glycerol fatty acid esters, glyceryl ethers, fatty acid diethanolamides and dimethyl amides, fatty acyl sarcosinates, alkyds and phospholipids. NOVASOMES® brand vesicles are preferred over traditional phospholipid based liposomes because they are more stable. NOVASOMES® brand vesicles are shaped like tiny balloons and formed by approximately 5-7 concentric membrane-like outer walls. They are typically 0.3-0.7 microns in diameter. They are stable in the presence of electrolytes and within a pH range of 2-10.

The topical preparation of the present invention may be provided in the form of a cream, lotion, solution, ointment, stick, patch or sleeve. The micro-encapsulation of the active ingredients in a preparation administered using a patch provides for longer lasting relief which does not feel as wet as typical topical analgesic patches. Optionally, the topical preparation may be administered in the form of a sleeve. As such, the sleeve may be used on joints such as the knees or wrist and other areas where a patch is difficult to keep in place. The material such as foam, hydrogel, nonwoven fabric, knitting or weaving of the patch or sleeve can be of any type, such as those commonly used in the art in connection with analgesic patches commonly available under the ICY HOT® brand from Chattem, Inc., under the DURA PATCH™ brand from U.S. Dermatologics, Inc., under the THERMO PATCH™ brand from LecTec Corporation, as the MENTHOLATUM PAIN PATCH™ from the Mentholatum Co., or as the TIGER BALM PATCH™ from Haw Par Healthcare, Ltd. Preferably, the sleeve material is light and flexible, or non-occulsive. In addition to holding the topical analgesic in place, another advantage of this invention is the added benefit of joint-specific applications such as joint-specific sleeves that provide support of a joint so that the pain is reduced as a result of compression, restricted range of motion, or mechanical support.

Referring now to the drawings, FIG. 1 is a top plan view of a preferred embodiment of the analgesic sleeve 10 according to the present invention. The sleeve 10 comprises an interior side 11 (shown in FIG. 4a); an exterior side 12; first and second welts 13a, 13b forming first and second end sections; first and second transition areas 14a, 14b interior of the end sections; and a body 20 having a therapeutic section such as patch 15 (shown in FIG. 4a) containing the active ingredients located on the interior side 11 of the sleeve 10. In a preferred use, the sleeve 10 essentially defines a lumen, having a wall formed of a flexible and elastic material with a patch area 15 that holds the micro-encapsulated topical analgesic. This sleeve 10 may be advantageously used on joints, such as the elbows, knees, ankles or wrists. The sleeve 10 is preferably knit from a combination of conventional yarns and specialty moisture management yarns. Fibers such as Sorbtek fibers from Unifi, Technofine fibers from Gelanots, and 4DG fibers from Fiber Innovative Technology, Inc. may be employed for moisture management. Typically, approximately one half of the circumference of a sleeve 10 will be composed of moisture management yarns and dosed or impregnated with the preparation comprising one or more topical analgesics, preferably in micro-encapsulated form.

FIG. 2 is a side plan end view of a preferred embodiment of an analgesic sleeve 10 according to the present invention. As in FIG. 1, the sleeve 10 defines a lumen, with a wall formed of a flexible material having a patch 15 that holds the micro-encapsulated topical analgesic. However, this sleeve 10 also has a thumb cavity 16 in first transition area 14a to secure the sleeve 10 in place over the hand and wrist. This configuration is particularly well-suited for the management of carpal tunnel syndrome, or repetitive motion injury of the forearm and wrist. The transition areas 14a, 14b and welts 13a, 13b at each end of the sleeve 10 are not generally comprised of moisture management yarns impregnated with analgesic preparations. The sleeves 10 illustrated are particularly sized for application to a wrist or small elbow, and additional sizes may be appropriately manufactured for knees, larger elbows, and to cover the usual range of dimensions of the human body. Thus, in a stretched or extended state, the lumen of the sleeves should accommodate a human extremity, such as an arm or leg. Furthermore, the moisture management system need not be yarn based, but may comprise a hydrogel, foam or other material held in place by a sleeve 10 of any suitable material including nonwovens, and especially stretchable nonwoven fabrics.

The sleeve 10 according to the present invention should fit snuggly against the skin so that the patch 15 is in sufficient contact with the affected area to be effective. If the sleeve 10 is too loose, the active ingredients of the patch 15 may not have sufficient contact with the affected area to be effective, and so in a relaxed state, the sleeve should effectively contact the patch to the affected area of the human extremity received within the sleeve. However, if the sleeve 10 is too tight it will cause discomfort to the affected area. For user comfort and support, a joint specific sleeve 10, when appropriately sized, may optionally be designed to provide a compression of about 3-40 mmHG and preferably about 7-30 mmHG. The presently preferred compression of the sleeve 10 is 10-15 mm Hg. The wearer may receive pain relief or improved joint function through action of analgesic preparations or compression, or both.

The sleeve 10 is preferably manufactured in various sizes to accommodate the widest range of human limb circumferences while holding the patch 15 of the sleeve 10 in contact with the skin. For example, a large sleeve 10 that expands to fit 8" to 24" in circumference is best used for knees, large ankles and elbows. A small sleeve 10 that expands to fit 5" to 12" in circumference is best used for wrists, small ankles and elbows.

A preferred embodiment of the sleeve 10 is formed from a continuously knit fabric bandage roughly in the form of a tube sock. The dimensions of a sleeve 10 according to this invention will typically provide a patch 15 area of at least about four (4) inches by two (2) inches in the relaxed condition or about five (5) inches by four (4) inches in the stretched condition. The longer welts 13a, 13b at each end of the sleeve 10 keep the garment from rolling down, slipping or moving when subjected to typical ranges of joint motion. For this purpose, the welts 13a, 13b have incorporated in them coated or uncoated spandex yarns or other similar elastic yarns.

The thumbhole cavities 16 allow the user to apply the sleeve 10 to the hand or the portion of the wrist closest to the hand by cutting the sleeve 10 as designated on the thumbhole cutout 18. The user may then orient the sleeve with her/his thumb through the thumb cavity 16. Two thumbhole cutouts 18 positioned 180 degrees from one another are provided on each sleeve 10 to allow the user to apply the sleeve 10 to either hand and orient the patch 15 to either the top or bottom portion of the hand or wrist. Alternatively, the sleeve 10 may be manufactured with two pre-cut reinforced thumb cavities 16 that may be used as a thumb hole. The reinforced thumb cavities 16 are preferably provided 180 degrees from one another to allow the user to apply the sleeve 10 to either hand and orient the patch 15 to either the top or bottom portion of the hand or wrist.

When made of knit fabric, the sleeve 10 is preferably constructed of 72% nylon and 10% spandex/lycra and 18% SORBTEK® brand synthetic fiber. The absorbent fiber is placed in the patch area 15 for maximum efficacy. This results in a flexible, breathable sleeve 10 that is comfortable for the user. The patch area 15 is centered longitudinally on the sleeve 10. The welts 13a, 13b are preferably knit with nylon and spandex yarns at the ends of the sleeve 10. Each welt 13 is preferably 22-28 mm long in its relaxed state. The two thumbhole cut outs 18 are preferably knit into the first transition area 14a of each sleeve 10 in a reinforced area which is approximately 20 mm long×25 mm wide. Preferably, black or colored yarn is stitched in the center of each thumbhole cut out 18 to guide the consumer to slit the sleeve 10 if a thumbhole is necessary.

The illustrated sleeve 10 may be knit on a 400 needle circular knitting machine. The knitting pattern on the body 20 of the sleeve 10 is a 3×2 rib pattern with three raised stitches and two recessed stitches forming longitudinal ribs in the sleeve. The patch area 15 contains the absorbent yarn, preferably SORBTEK™ color PMS 30054 (blue)/Unifi color 4895H Sorbtek Blue, plated with nylon. The knitting pattern of the patch area 15 is an 8×7 rib pattern. The welts 13a, 13b are knit with nylon and 210 denier Spandex yarns at each end of the sleeve 10. Each welt 13a, 13b is about an inch long in the relaxed state. Welts 13a, 13b are knit in a 1×1 ribbed pattern. In the preferred embodiment of a smaller sleeve for use on wrists and small elbow joints, there are two thumbhole cut outs 18 knit into the transition areas 14 of each sleeve 10 in a reinforced area approximately 20 mm long×25 mm wide. A line of knitting of colored or black yarn is put in the center of each thumbhole cut out 18 to show the consumer where to slit the sleeve 10 if the thumbhole is desired. The line of knitting is about 15 mm long in the transverse direction across the sleeve 10, and is centered longitudinally and transversely within the reinforced thumbhole cut outs 18. The top edge of the thumbhole cut outs 18 is 33 mm from the edge of the sleeve 10 including the welt 13. Both thumbhole cut outs 18 are positioned at the same end of the sleeve 10. The longitudinal centerline of the thumbhole cut outs 18 is aligned with the longitudinal edge of the patch 15 on each side of the patch 15. Thumbhole cut out 18 knitting pattern is a positive stitch.

After a knit sleeve 10 has been manufactured, the sleeve 10 is preferably positioned with its interior 11 facing outward, and the exterior surface 12 being flatly collapsed against itself. An insert 22, preferably made from about 10 ml PVC, is placed between the upper and lower portions of the exterior surface 12 to provide shape to the flattened and inside-out sleeve 10. When positioned in this fashion, the patch area 15 should be substantially on the top side of the PVC insert 22, and the portion of the body 20 without the absorbent yarn forming the patch area should be positioned beneath the PVC insert 22. The PVC insert 22 is positioned in this fashion beneath the patch area 15 of the body 20 of the sleeve 10 to facilitate the dispensing of the topical analgesic, in liposome form, onto the patch, and to some extent to keep the topical analgesic contained and concentrated. Even so, there is generally some migration of the topical analgesic into yarns other than those forming the patch area 15. A typical dosing of about two grams of topical analgesic in liposome form is applied onto the patch area 15. The particular formulation of the topical analgesic and materials used for the patch area 15 may affect the preferred dosage amounts. For a smaller sleeve, the PVC insert 22 is preferably about 10" long and 2½" wide at its center and tapered at both ends to a 1¾" straight end perpendicular to the sides. The PVC insert 22 may be perforated or otherwise scored across the center to allow for easier folding. This permits the sleeve 10 to be readily folded transversely across the center along the perforations in the PVC insert 22, with the patch area 15 treated with topical analgesic forming the inside of the fold. When folded, the ends of the sleeve 10 should match, and the patch area 15 should be folded upon itself. The sleeve 10 is then inserted into a pouch and sealed to maintain the active ingredients. The pouch is preferably formed of a plastic and foil laminate film for this purpose, and for consumer convenience.

Figure 3A:
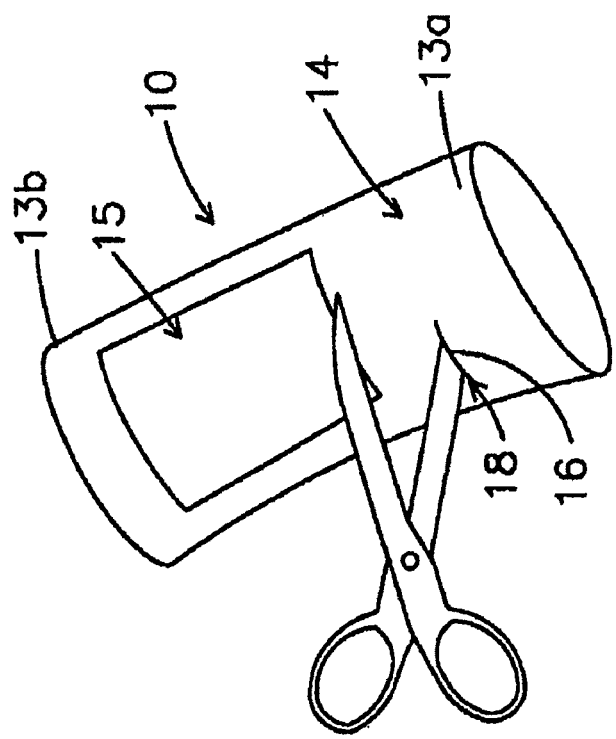
Figure 5:
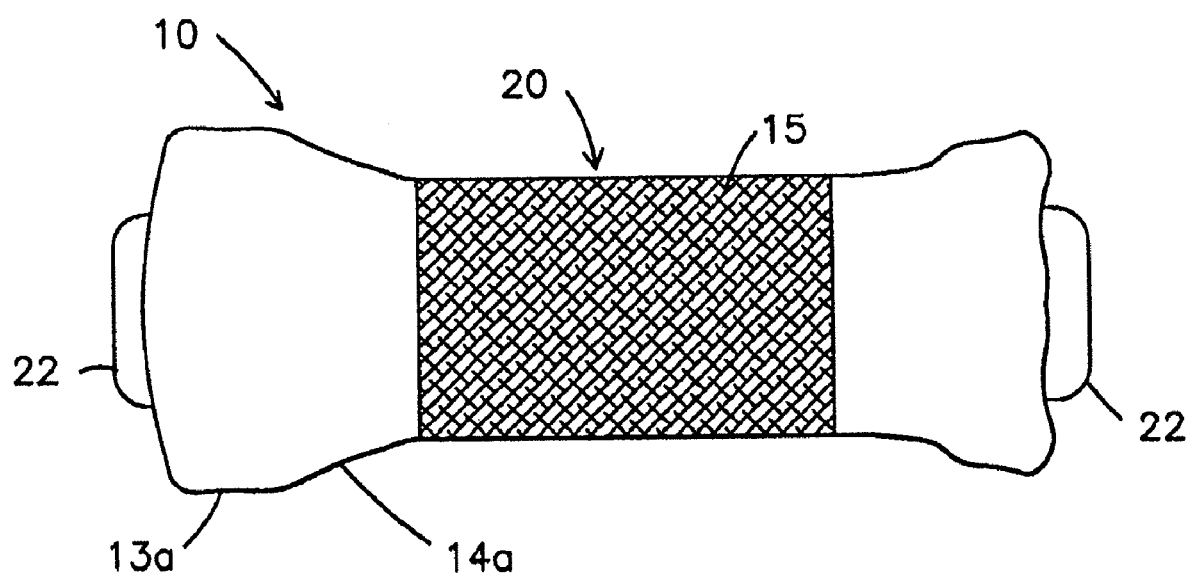
FIG. 5 illustrates a flattened knit sleeve with an insert.

Referring now to FIGS. 3a, 3b, 4a, 4b and 4c in the preferred embodiment, the sleeve 10 is packaged and reaches the consumer both folded and "inside out." Thus, when the sleeve 10 is removed from its pouch and unfolded, the portion of the sleeve 10 that contains the patch 15 treated with analgesic is inside out on the "interior" side 11 of the sleeve 10 and visible to the consumer. When applying a sleeve 10 to the wrist, the consumer first removes the PVC insert 22, and then cuts a slit on a thumbhole cut out 18 as shown in FIG. 3a, thereby creating a thumb hole 16. The consumer then applies the sleeve 10 by pulling the thumb hole 16 over the thumb and the sleeve 10 over the affected area while turning the sleeve 10 inside out so that the patch area 15 is positioned on the area of the wrist where the analgesic is desired.

As shown in FIGS. 4a, 4b and 4c, when applying the sleeve 10 to the arm, elbow, leg, knee or ankle, the consumer first pulls the sleeve 10 adjacent to the affected area while the portion of the sleeve 10 that contains the analgesic treated patch area 15 is inside out on the "interior" side 11 of the sleeve 10 and visible to the consumer. The first welt 13a of the sleeve is positioned next to the affected area, and the remainder of the sleeve 10 is opposite the first welt 13a from the affected area as shown in FIG. 4a. Once the sleeve 10 is in position, the consumer rolls the second welt 13b of the sleeve 10 over, leaving the first welt 13a very nearly in the same position while the inside out sleeve is reversed so that the portion of the sleeve 10 that contains the analgesic patch 15 is left on the interior side 11 of the sleeve 10 and is placed over the affected area coming into contact with the skin as shown in FIGS. 4b and 4c. It is anticipated that in many cases the affected area will be in proximity to joints such as wrists, elbows, knees and ankles.

The present sleeve design may also be utilized in wound care to apply medication to a wound, particularly on the arms and legs of a patient.

The topical analgesics of the invention are further illustrated by means of the following illustrative embodiments, which are provided for the purpose of illustration only and are not meant to limit the invention to the particular components and amounts disclosed. The following examples show composition of preferred embodiments of topical analgesic formulations.

Example 1 below discloses a micro-encapsulated topical preparation comprising 16% menthol Novasomes lipid vesicle encapsulation solution. The solution is a white, smooth solution with the following specifications, stability data and ingredients:

EXAMPLE 1

| Specifications |
|---|
| pH = 5.0-8.0 |
| Visc = 1000-3000 cps |
| Assay Menthol = 15.7%-16.8% |
| Spec gravity = 0.95000-0.9900 |

| Ingredients | Percent By Weight |
|---|---|
| Deionized Water | 48.0-50.0 |
| Menthol USP | 15.0-17.0 |
| Diisopropyl Adipate | 12.0-14.0 |
| Glyceryl Monostearate | 8.0-10.0 |
| Diethylene Glycol mono ethyl ether | 4.0-6.0 |
| Polysorbate 80 | 2.0-3.0 |
| Glyceryl Dilaurate | 2.0-3.0 |
| Soya sterol | 1.0-3.0 |
| PEG-150 stearate | 0.5-1.5 |
| Cetyl Alcohol | 0.5-1.5 |
| Phenoxyethanol | 0.3-0.5 |
| Methylparaben | 0.1-0.3 |
| Disodium EDTA | 0.05-0.15 |
| Xanthan Gum | 0.005-0.01 |

Example 2 below discloses a micro-encapsulated topical analgesic concentrate comprising 32% menthol Novasomes lipid vesicle encapsulation solution. The solution is white, smooth solution with the following specifications, stability data and ingredients

EXAMPLE 2

| Specifications |
|---|
| pH = 6.5-8.5 |
| Visc = 5000-8000 cps |
| Assay Menthol = 30.4%-33.86% |
| Spec gravity = 0.9555-0.9755 |

| Ingredients | Percent By Weight |
|---|---|
| Deionized Water | 25.0-27.0 |
| Menthol USP | 31.0-33.0 |
| Diisopropyl Adipate | 15.0-17.0 |
| Diethylene Glycol mono ethyl ether | 4.0-6.0 |
| Glyceryl Monostearate | 2.5-3.5 |

-continued

| Ingredients | |
|---|---|
| Polysorbate 80 | 2.0-3.0 |
| Glyceryl Dilaurate | 2.0-3.0 |
| PEG-150 stearate | .5-1.5 |
| Cetyl Alcohol | .5-1.5 |
| Soya sterol | .4-.6 |
| Phenoxyethanol | .3-.5 |
| Methylparaben | .1-.3 |
| Disodium EDTA | .05-.15 |
| Xanthan Gum | 0.005-.01 |

This concentrate is intended to be diluted to the level set by the FDA Tentative Monograph described above.

Yet another similar Novasomes lipid vesicle encapsulation formulation is disclosed in Example 3 below with both menthol and menthyl lactate:

| Ingredients | Percent by Weight |
|---|---|
| Deionized Water | 38.0-42.0 |
| Menthol USP | 15.0-17.0 |
| Menthyl Lactate | 15.0-17.0 |
| Diisopropyl Adipate | 12.0-17.0 |
| Glyceryl Monostearate | 2.5-7.0 |
| Diethylene Glycol mono ethyl ether | 2.5-5.0 |
| Glyceryl Dilaurate | 2.0-3.0 |
| Polysorbate 80 | 1.5-2.5 |
| PEG-150 stearate | 0.5-1.5 |
| Soya sterol | 0.4-0.6 |
| Cetyl Alcohol | 0.4-1.5 |
| Phenoxyethanol | 0.3-0.5 |
| Methylparaben | 0.1-0.3 |
| Disodium EDTA | 0.05-0.15 |
| Xanthan Gum | 0.005-0.1 |
| Glycerin | 0.1-0.25 |
| Citric Acid (optional) | about 0.05 |

While preferred embodiments of the invention have been described above, it is to be understood that any and all equivalent realizations of the present invention are included within the scope and spirit thereof. Thus, the embodiments depicted are presented by way of example only and are not intended as limitations upon the present invention. While particular embodiments of the invention have been described and shown, it will be understood by those skilled in the art that the present invention is not limited thereto since many modifications can be made.

We claim:

1. A sealed pouch containing a sleeve of the type having a first end and second end and a sleeve wall extending therebetween and defining a lumen, and wherein the sleeve wall is elastically stretchable and has an interior side with a therapeutic section having moisture management system dosed with a pharmaceutical composition, the sleeve being flattened and positioned in an inside-out orientation so that the interior side with a therapeutic section is outwardly facing; and an insert being received within the lumen.

2. The sealed pouch of claim 1 wherein the insert is scored to facilitate folding.

3. The sealed pouch of claim 1 wherein the sleeve is folded so that the therapeutic section is folded upon itself.

4. The sealed pouch of claim 1 wherein the pharmaceutical composition comprises a micro-encapsulated active ingredient.

5. The sealed pouch of claim 1 wherein the sleeve is formed from the group of knit fabrics and stretchable nonwoven fabrics.

6. The sealed pouch of claim 1 wherein the pharmaceutical composition comprises a topical analgesic.

7. The sealed pouch of claim 1 wherein the pouch is formed of a plastic and foil laminate film.

8. The sealed pouch of claim 1 wherein the sleeve wall provides compression of between about 7 and about 30 mmHG upon a human extremity received in the lumen.

9. The sealed pouch of claim 1 wherein the moisture management system comprises moisture management yarns.

10. The sealed pouch of claim 1 wherein the moisture management system is selected from the group of hydrogels and foams.

11. The sealed pouch of claim 4 wherein the active ingredient is selected from the group consisting of local anesthetics, anti-inflammatories, counter-irritants and mixtures thereof.

12. The sealed pouch of claim 11 wherein the local anesthetic is selected from the group consisting of lidocaine.

13. The sealed pouch of claim 11 wherein the anti-inflammatory is selected from the group consisting of salicylates and NSAIDS.

14. The sealed pouch of claim 11 wherein the counter-irritant is selected from the group consisting of capsaicin, menthol, oil of wintergreen, camphor, eucalyptus, mustard plasters and terpentine oil.

15. The sealed pouch of claim 4 wherein the active ingredient comprises menthol and menthol derivatives.

16. The sealed pouch of claim 4 wherein the active ingredient comprises between about 1.25% to 16% by weight menthol.

17. The sealed pouch of claim 4 wherein the active ingredient comprises between about 0.5% to 20% by weight menthyl lactate.

18. The sealed pouch of claim 4 wherein the active ingredient comprises between about 0.025% to 0.25% by weight capsaicin.

19. The sealed pouch of claim 4 wherein the active ingredient is micro-encapsulated utilizing a liposome technology.

* * * * *